(12) United States Patent
Abraham

(10) Patent No.: US 7,135,298 B2
(45) Date of Patent: Nov. 14, 2006

(54) SCREENING ASSAY FOR AGENTS THAT ALTER TARGET OF RAPAMYCIN ACTIVITY

(75) Inventor: Robert T. Abraham, San Diego, CA (US)

(73) Assignee: The Burnham Institute for Medical Research, La Jolla, CA (US)

( * ) Notice: Subject to any disclaimer, the term of this patent is extended or adjusted under 35 U.S.C. 154(b) by 181 days.

(21) Appl. No.: 10/401,058

(22) Filed: Mar. 26, 2003

(65) Prior Publication Data

US 2004/0191836 A1    Sep. 30, 2004

(51) Int. Cl.
G01N 33/53    (2006.01)
G01N 33/567    (2006.01)
C12Q 1/33    (2006.01)
C12P 1/00    (2006.01)
C12N 9/00    (2006.01)

(52) U.S. Cl. .................... 435/7.1; 435/4; 435/7.2; 435/7.21; 435/7.71; 435/7.91; 435/21; 435/41; 435/183; 435/325; 436/2; 436/86; 436/174; 436/504

(58) Field of Classification Search ............... 424/1.11, 424/130.1, 143.1, 156.1, 184.1, 192.1, 278.1, 424/404; 435/4, 243, 244, 7.1, 7.2, 7.21, 435/7.71, 7.91, 21, 41, 183, 325; 436/2, 436/86, 174, 501
See application file for complete search history.

(56) References Cited

U.S. PATENT DOCUMENTS 5,759,787 A * 6/1998 Strulovici .................... 435/7.4

OTHER PUBLICATIONS

Brunn et al. (1997). J. of Biol. Chem. vol. 272(51): 32547-32550.*
Brunn et al. (1997). Science. vol. 277:99-101.*
Burnett et al. (1998). P.N.A.S. vol. 95: 1432-1437.*
McMahon et al. (2002). Mol. Cell Biol. vol. 22 (21): 7428-7438.*
Nave et al. (1999). Biochem.J. vol. 344: 427-431.*
Polakiewicz, et al.,—Opioid Receptor Activates Signaling Pathways Implicated in Cell Survival and Translational Control*, J. Biol. Chem. 273: 23534 (1998).
Powers, et al., Regulation of Ribosome Biogenesis by the Rapamycin-sensitive TOR-signaling pathway in Saccharomyces cerevisiae, Mol. Biol. Cell 10: 987 (1999).
Raught, et al,. The target of rapamycin (TOR) proteins,PNAS 98: 7037 (2001).
Sabatini, et al., Interaction of RAFT1 with Gephyrin Required for Rapamycin-Sensitive Signaling, Science 284: 1161 (1999).
Sabers CJ. et al. Isolation of a protein target of the FKBP12-rapamycin complex in mammalian cells. Journal of Biological Chemistry 270(2):815-22, 1995.
Schalm, Stefanie S. and John Blenis, Identification of a Conserved Motif Required for mTOR Signaling; Current Biology 2002: 632-639.

(Continued)

Primary Examiner—Lynette R. F. Smith
Assistant Examiner—J. Hines
(74) Attorney, Agent, or Firm—Catalyst Law Group, APC

(57) ABSTRACT

The present invention provides an assay for the identification of agents which can modulate TOR-mediated phosphorylation of substrate proteins. The assays of the invention utilize substrate proteins whose amino acid sequence contains the Ser/Thr motif recognized by TOR. Naturally occurring TOR which may be used in the methods of the invention include TOR isolated from a variety of species, particularly mammalian tissues.

11 Claims, 4 Drawing Sheets

Western Blot

PhosphoImager

OTHER PUBLICATIONS

Schlam, Stefanie S. et al., TOS Motif-Mediated Raptor Binding Regulates 4E-BP1 Multisite Phosphorylation and Function; Current Biology 2003 13: 797-806.
Scheper, et al., Eukaryotic Initiation Factors-4E and -4F Stimulate 5' cap-dependent as well as internal initiation of protein synthesis*, J. Biol. Chem. 267: 7269 (1992).
Schmelzle, et al. TOR, a central controller of cell growth, Cell 103: 253 (2000).
Schmidt, et al., The TOR nutrient signalling pathway phosphorylates NPR1 and inhibits turnover of the tryptophan permease, EMBO J. 17: 6924 (1998).
Scott, et al., Evidence of insulin-stimulated phosphorylation and activation of the mammalian target of rapamycin mediated by a protein kinase B signaling pathway, PNAS 95: 7772 (1998).
Sekulic, et al., A direct linkage between the Phosphoinositide 3-Kinase-AKT Signaling pathway and the mammalian target of rapamycin in mitogen-stimulated and transformed cells, Cancer Res. 60: 3504 (2000).
Shamji, et al., Partitioning the transcriptional program induced by rapamycin among the effectors of the Tor proteins, Curr. Biol. 10: 1574 (2000).
Shigemitsu, et al., Regulation of Translational Effectors by Amino Acid and Mammalian Target of Rapamycin Signaling Pathways, J. Biol. Chem. 274: 1058 (1999).
Sousa A.G., Van Langenhove G. and Falotico R. et al. (2001) Sustained suppression of neointimal proliferation by sirolimus-eluting stents: one-year angiographic and intravascular ultrasound follow-up. Circulation 104:2007-2011.
Tibbets, Randall S. and Abraham, Robert T., PI3K-Related Kinases Roles in Cell-Cycle Regulation and DNA Damage Responses, Signaling Networks and Cell Cycle Control: The Molecular Basis of Cancer and Other Diseases Humana Press Inc. (2000).
Vlahos et al., JA Specific Inhibitor of Phosphatidylinositol 3-Kinase, 2-(4-Morpholinyl)-8-phenyl-4-benzopyran-4-one (LY294002). Biol. Chem. 269: 5241 (1994).
Welsh, et al.,Activation of Microtubule-Associated Protein Kinase (Erk) and p70 S6 Kinase by D2 Dopamine Receptors, J. Neurochem. 70: 2139 (1998).
Zhang, H., Stallock, J. P., NG, J. C., Reinhard, C. & Neufeld, T. P., Regulation of cellular growth by the Drosophila target of rapamycin dTOR, Genes Dev. 14:2712 (2000).
Abraham, R. T., and Wiederrecht, G. J. Immunopharmacology of rapamycin. Annu. Rev. Immunol. 14: 483 (1996).
Abraham, R.T. Identification of TOR Signaling Complexes: More TORC for the Cell Growth Engine. Cell 111: 9 (2002).
Arcaro et al., Biochem. J. 296: 297 (1993) Wortmannin is a potential phosphatidylinositol 3-kinase inhibitor: the role of phosphatidylinositol 3,4,5-triphosphate in neutrophil responses University of Fribourg, Rue du Musee 5. CH-1700 Fribourg, Switzerland.
Barbet, N. C., Schneider, U., Heillwell, S. B., Stansfield, I., Tuite, M. F. & Hall, M. N. Mol. Biol. Cell 7: 25 (1996) TOR Controls Translation Initiation and Early G1 Progression in Yeast (1996).
Beck, et al., The TOR signalling pathway controls nuclear localization of mutrient-regulated transcription factors, Nature (London) 402: 689 (1999).
Beretta, L., Gingras, A.-C., Svitkin, Y. V., Hall, M. N. and Sonenberg, N., Rapamycin blocks the phosphorylation of 4E-BP1 and inhibits cap-dependent initiation of translation. EMBO J. 15: 658 (1996).
Berset, et al., The TOR signal transduction pathway regulates the stability of translation initiation factor eIF4G in the yeast *Saccharomyes cerevisiae*, Proc. Natl. Acad. Sci. USA 95: 4264 (1998).
Blommaart, E. F., Luiken, J. J., Bloomaart, P. J., Van Woerkom, G. M. & Meijer, A. J., Phosphorylation of Ribosomal Protein S6 is inhibitory for autophagy in isolated rat hepatocytes* J. Biol. Chem. 270: 2320 (1995).
Brown, E. J., et al., A mammalian protein targeted by G=1 arresting rapamycin-receptor complex S. L. Nature (London) 369: 756 (1994).

Brunn, G. J., et al. Direct inibition of the signaling functions of the mammalian target of rapamycin by the phosphoinositide 3-kinase inhibitors, wortmannin and LY294002. EMBO J. 15:5256 (1996).
Brunn, G. J., et al. The mammalian target of rapamycin phosphorylates sites having a (Ser/Thr)-Pro motif and is activated by antibodies to a region near its COOH-terminus. J. Bio. Chem. 272(51):32547 (1997).
Brunn, G. J., et al.Phosphorylation of the translational repressor PHAS-I by the mammalian target of rapamycin. Science. 277(5322):99 (1997).
Burnett, P. E., Barrow, R. K., Cohen, N. A., Snyder, S. H. and Sabatini, D. M. RAFT1 phosphorylation of the translational regulators p70 S6 kinase and 4E-PB1. Proc. Natl. Acad. Sci. USA 95: 1432 (1998).
Casadio, A., Martin, K. C., Giustetto, M., Zhu, H., Chen, M., Bartsch, D., Bailey, C. H. & Kandel, E. R., A transient, neuron-wide form of CREB-Mediated long-term facilitation can be stabilized at specific synapses by local protein synthesis, Cell 99:221 (1999).
Chan, et al., A chemical genomics approach toward understanding the global functions of the target of rapamycin protein (TOR) PNAS USA 97: 13227 (2000).
Di Como, C. J. & Arndt, K. T. Genes Dev. 10:1904 Nutrients, via the Tor proteins, stimulate the association of Tap42 with type 2A phosphatases (1996).
Dumont et al., Distinct mechanisms of suppression of murine T cell activation by the related macrolides FK-506 and rapamycin, J. Immunol. 144: 251 (1990).
Essrich, et al., Postsynaptic clustering of major CABA receptor subtypes requires the 2 subunit and gephyrin, Nat. Neurosci. 1: 563 (1998).
Gingras, A. C., Raught, B., and Sonenberg, N. Regulation of translation initiation by FRAP/mTOR. Genes Dev. 15:807 (2001).
Glass, David J., Signalling pathways that mediate skeletal muscle hypertrophy and atrophy, Nature Cell Biol. 5(2):87 (2003).
Hidalgo, Manuel and Rowinsky, Eric K., The rapamycin-sensitive signal transduction pathway as a target for cancer therapy, Univ. of Texas Oncogene (2000) 19, 6680-6686.
Harris et al., The Arabidopsis Homolog of Yeast TAP42 and Mammalian 4 Binds to the catalytic subunit of protein phosphatase 2A and is induced by chilling., Plant Physiol. 121: 609(1999).
Haystead, T. A. J., Haystead, C. M. M., Hu, C., Lin, T.-A. and Lawrence, J. C. Jr. Phosphorylation of PHAS-I by mitogen-activated protein (MAP) kinase. Identification of a site phosphorylated by MAP kinase in vitro and in response to insulin in adipocytes. J. Biol. Chem.
Huang S. Houghton PJ. Inhibitors of mammalian target of rapamycin as novel antitumor agents: from bench to clinic. Current Opinion in Investigational Drugs. 3(2):295-304, 2002.
Hudson et al., Regulation of Hypoxia-Inducible factor 1 Expression and Function by the Mammalian Target of Rapamycin, Mol. Cell Bio.l 22: 7004 (2002).
Inui, et al., Molecular cloning of a cDNA clone encoding a phophprotein compoonent related to the lg receptor-mediated signal transduction, J. Immunol. 154: 2714 (1995).
Jeffries et al., Rapamycin suppresses 5'TOP mRNA translation through inhibition of p70 s6k, EMBO J. 15: 3693 (1997).
Jiang, et al., Tor proteins and protein phosphatase 2A reciprocally regulate Tap42 in controlling cell growth in yeast, EMBO J. 18: 2782 (1999.
Khan, et al., Serotonin Activates S6 Kinase in a Rapamycin-Sensitive Manner in Aplysia Synaptosomes, Neurosci. 21: 382 (2001.
Kim, et al., Autophagy, Cytoplasm-to-vacuole targeting pathway, and pexophagy in yeast and mammalian cells, Annu. Rev. Biochem. 69: 303 (2000).
Kirsch, et al., Gephyrin antisense oligonucleotides prevent glycine receptor clustering in spinal neurons. Nature (London) 366: 745(1993).
Klionsky, et al., Autophagy as a Regulated Pathway of Cellular Degradation, Science 290: 1717 (2000).
Klionsky, et al., Vacuolar Import of Proteins and Organelles From The Cytoplasm, Annu. Rev. Cell Dev. Biol. 15: 1 (1999).

Kunz et al., Target of rapamycin in Yeast, TOR2, Is an essential phosphatidylinositol kinase homolog required for G1 progression. Cell 73: 585 (1993).

Leicht, et al., Okadaic acid induces cellular hypertrophy in AKR-2B fibroblast: Involvement of the p70S6 kinase in the onset of protein and rRNA synthesis. Cell Growth Differ 7: 1199 (1996).

Mahajan, Int. J. Modulation of Transcription of rRNA genes by rapamycin. Int. J. Immunopharmacol. 16: 711 (1994).

McMahon et al., The Rapamycin-Binding Domain Governs Substrate Selectivity by the Mammalian Target of Rapamycin, Mol. Cell. Biol. 22: 7428 (2002).

Morice WG. Brunn GJ. Wiederrecht G. Siekierka JJ. Abraham RT. Rapamycin-induced inhibition of p34cdc2 kinase activation is associated with G1/S-phase growth arrest in T lymphocytes.Journal of Biological Chemistry 268(5):3734-8, 1993.

Nakanishi et al., Wortmannin, a Microbial Product Inhibitor of Myosin Light Chain Kinase*, J. Biol. Chem. 267: 2157 (1992).

Nave', et al., Mammalian target of rapamycin is a direct target for protein kinase B: Identification of a convergence point for opposing effects of insulin and amino-acid deficiency on protein translation. Biochem. J. 344:427 (1999).

Noda, et al., Tor, a Phosphatidylinositol Kinase Homologue, Controls Autophagy in Yeast, J. Biol. Chem. 273: 3963 (1998).

Onda et al., Expression and Chromosomal Localization of the Human 4/IGBP1 Gene, the structure of which is closely related to the yeast TAP42 protein of the rapamycin sensitive signal transduction pathway. Genomics 46: 373 (1997.

Peterson, et al., FKBP12-Rapamycin-associated Protein (FRAP) Autophosporylates at Serine 2481 under translationally repressive conditions.*, J. Biol.Chem. 275: 7416 (2000).

Powis et al., Wortmannin, a Potent and Selective Inhibitor of Phosphatidylinositol-3kinase. Cancer Res. 54: 5241 (1994).

Sarkaria JN. et al. Inhibition of phosphoinositide 3-kinase related kinases by the radiosensitizing agent wortmannin. Cancer Research. 58(19):4375-82, 1998.

Saunders et al., Rapamycin in transplantation: A review of the evidence. Kidney Int., 59: 3 (2001).

Scott, et al., Evidence of insulin-stimulated phosphorylation and activation of the mammalian target of rapamycin mediated by a protein kinase B signaling pathway, PNAS 95: 7772 (1998.

Tibbets, Randall S. and Abraham, Robert T. P13K-Related Kinases Roles in Cell-Cycle Regulation and DNA Damage Responses, Signaling Networks and Cell Cycle Control: The Molecular Basis of Cancer and Other Diseases Humana Press Inc.

* cited by examiner

SCREENING ASSAY FOR AGENTS THAT ALTER TARGET OF RAPAMYCIN ACTIVITY

STATEMENT REGARDING FEDERALLY SPONSORED RESEARCH

This invention was made in part with the United States government support under Grant Numbers CA76103 and CA97950 from the NIH. The U.S. government may have certain rights in this invention.

FIELD OF THE INVENTION

This invention relates to methods for detecting modulators of the Target of Rapamycin (TOR) protein, and to a fusion protein useful in such methods.

BACKGROUND OF THE INVENTION

The Target of Rapamycin (TOR) is a highly conserved protein kinase found in both prokaryotes and eukaryotes. TOR proteins are members of the phosphoinositide (PI) 3-kinase related kinase (PIKK) family, which includes mammalian ATM, ATR, and DNA-PK (Tibbetts, and Abraham, *Signaling Networks and Cell Cycle Control: The Molecular Basis of Cancer and Other Diseases*, 5:267 (2000)). Like other PIKK family members, the TORs are large polypeptides (280–300 kDa) that bear a carboxy-terminal region with sequence similarity to the catalytic domains of PI3-kinases (PI3K) (Abraham et al., *Annu. Rev. Immunol.* 14: 483 (1996)). PIKK family members possessing active kinase domains phosphorylate proteins on serine or threonine residues. The consensus phosphorylation site for all PIKK family members (except the TORs) is serine/threonine followed by glutamine at the +1 position. The preferred sequence motif for the TORs remains unclear; however, known in vitro substrates contain serine/threonine followed by proline or a hydrophobic amino acid at the +1 position. The lack of a consensus motif for substrate recognition by TOR kinases hints that these PIKK family members may rely on an alternative mechanism for substrate identification or regulation in intact cells. (Abraham, *Cell* 111: 9 (2002)).

Several lines of evidence suggest that the TOR proteins function in a nutrient-sensing checkpoint control capacity. Both TOR and PI3K signaling are required for the activation (or inactivation) of several downstream effector proteins. However, whether TOR activity is regulated by PI3K, or whether the two signaling pathways function independently, is unknown. Overexpression of a membrane-targeted Akt/PKB protein (a downstream effector of PI3K) in mammalian cells leads only to a modest increase (or no change) in TOR kinase activity (as assayed in vitro), and moderately increases TOR autophosphorylation in vivo, as assessed with the S2481 phospho-specific antibody (Scott, et al., *PNAS* 95: 7772 (1998); Peterson, et al., *J. Biol.Chem.* 275: 7416 (2000); Sekulic, et al., *Cancer Res.* 60: 3504 (2000)).

Rapamycin is a bacterial macrolide with antifungal and immunosuppressant activities (Dumont et al., *J. Immunol.* 144: 251 (1990)). For example, rapamycin forms a complex with the immunophillin FKBP12 which then inhibits the kinase activity of TOR (Brown et al., *Nature* 369: 756 (1994); Kunz et al., *Cell* 73: 585 (1993)). Rapamycin treatment of cells leads to the dephosphorylation and inactivation of the cell-growth-promoting P70 S6 Kinase (Jeffries et al., *EMBO J.* 15: 3693 (1997); Beretta et al., *EMBO J.* 15: 658 (1996); Raught et al, *PNAS* 98: 7037 (2001)). In addition to rapamycin, wortmannin and LY294002 have also been shown to affect TOR signaling. Wortmannin is an active site inhibitor that abolishes TOR autophosphorylation. LY294002 blocks PI3K dependant Akt phosphorylation and kinase activity and inhibits TOR autophosphorylation as well. (Brunn et al, *EMBO J.* 15: 5256 (1996)). Rapamycin, wortmannin and LY294002 are commercially available from Cell Signaling Technology, Beverly, Mass., as Cat. Nos. 9904, 9951 and 9901, respectively.

Inactivation of the TOR proteins, or rapamycin treatment, mimics nutrient deprivation in yeast, Drosophila, and mammalian cells (Zhang, et al, *Genes Dev.* 14: 2712 (2000); Sekulic, et al., *Cancer Res.* 60: 3504 (2000); Navé, et al., *Biochem. J.* 344: 427 (1999); Barbet, et al, *Mol. Biol. Cell* 7: 25 (1996)). Thus, a current working model for TOR signaling proposes that these kinases relay a permissive signal to downstream targets only in the presence of sufficient nutrients to fuel protein synthesis. Because the TOR proteins appear to function in a coregulatory capacity with other conventional, linear signaling pathways, a passive nutrient sufficiency signal may be combined with stimulatory signaling from a second pathway to coordinate cellular processes that require the uptake of nutrients. The absence of either signal is predicted to prohibit activation of downstream targets. (Raught, et al,. *PNAS* 98: 7037 (2001)).

It is believed that TOR signaling is affected through a combination of repression of phosphatase activity, and direct phosphorylation of downstream targets. Genetic screening in *Saccharomyces cerevisiae* has identified a phosphatase-associated protein (Tap42p), as one component of a rapamycin-sensitive signaling pathway (Schmelzle, et al., *Cell* 103: 253 (2000); Di Como, et al., *Genes Dev.* 10: 1904 (1996)). Tap42p phosphorylation is modulated by TOR signaling, which in turn regulates Tap42p interaction with phosphatases, such as PP2A (Jiang, et al., *EMBO J.* 18: 2782 (1999); Schmidt, et al., *EMBO J.* 17: 6924 (1998); Beck, et al., *Nature (London)* 402: 689 (1999); Di Como, et al., *Genes Dev.* 10: 1904 (1996); Jiang, et al., *EMBO J.* 18: 2782 (1999)). Tap42 orthologs are found in Arabidopsis (Harris, et al., *Plant Physiol.* 121: 609 (1999)), Drosophila, (GenBank accession number AAF53289), and mammalian cells (Inui, et al., *J. Immunol.* 154: 2714 (1995); Onda, et al., *Genomics* 46: 373 (1997)). In mammals, the B cell receptor binding protein α4 (a.k.a Ig binding protein 1, IGBP1) is the ortholog of Tap42p (Inui, et al., *J. Immunol.* 154: 2714 (1995); Onda, et al., *Genomics* 46: 373 (1997)).

TOR acts directly on other downstream targets, regulating the balance between protein synthesis and protein degradation in response to nutrient quality and quantity. TOR proteins regulate: (i) initiation and elongation phases of translation; (ii) ribosome biosynthesis; (iii) amino acid import; (iv) the transcription of numerous enzymes involved in multiple metabolic pathways; (v) autophagy, and (vi) expression of hypoxia-induced factor (HIF)-1 in oxygen-deprived cells (for a review see; Raught, et al., *PNAS* 98: 7037 (2001); see also, Hudson et al., *Mol. Cell Bio.l* 22: 7004 (2002)).

TOR signaling, in combination with the PI3K pathway, initiates the translation of rapamycin-sensitive mRNAs. In the presence of sufficient nutrients to fuel protein synthesis, TOR and PI3K signaling activate the S6Ks, and one or more unknown kinases, to effect phosphorylation of the ribosomal S6 protein, eIF4B, eIF4GI, and the 4E-BPs. TOR signaling has been reported to inhibit eEF2 phosphorylation (possibly via inhibition of the eEF2 kinase), thus, increasing elongation rates (Raught, et al., *PNAS* 98: 7037 (2001)).

Inhibition of TOR activity in *S. cerevisiae* potently represses translation initiation, concomitant with polysome disaggregation and cell cycle arrest in G.sub. 1 (Barbet, et al., *Mol. Biol. Cell* 7: 25 (1996)). The mechanism for this translational repression is not understood, but could be due, at least in some strains, to the degradation of the initiation factor eIF4G (Berset, et al., *Proc. Natl. Acad. Sci. USA* 95: 4264 (1998); Powers, et al., *Mol. Biol. Cell* 10: 987 (1999)).

In addition to its effect on the phosphorylation state of proteins involved in translational control, TOR signaling regulates an abundance of the components of the translation machinery, at both the transcriptional and translational levels. Through the S6Ks, TOR signaling regulates the translation of ribosomal protein mRNAs in mammalian cells (Leicht, et al., *Cell Growth Differ.* 7: 1199 (1996); Mahajan, *Int. J. Immunopharmacol.* 16: 711 (1994)). Transfer of cultured mammalian cells from standard growth medium into amino acid and/or glucose-free medium leads to rapid dephosphorylation of two TOR substrates, S6K1 (p70 S6 kinase) and 4EBP1 (PHAS-I) (Gingras et al., *Genes Dev.* 15: 807 (2001)). In the dephosphorylated state, S6K1 activity is repressed in starved cells, and nutrient stimulation leads to its phosphorylation and activation.

Activated S6K1 stimulates ribosome biogenesis, upregulating the translational capacity of the cell. Similarly, 4E-BP1 binds avidly to eIF-4E, thereby suppressing cap-dependent protein synthesis. Restoration of nutrients provokes multisite phosphorylation of 4E-BP1 by TOR (and possibly other protein kinases), release of eIF-4E, and resumption of cap-dependent translation. Activators of TOR could also be useful in the therapy of muscle degeneration induced by diseases such as cancer or muscular dystrophy (for review, see Glass, *Nature Cell Biol.* 5(2):87 (2003)). Thus TOR is a central component of a rapamycin-sensitive signaling pathway that coordinates protein synthesis with glucose and amino acid availability. (Abraham, *Cell* 111: 9 (2002)).

In both yeast and mammalian cells, TOR signaling regulates autophagy. When nutrient levels are low, eukaryotic cells degrade cytoplasmic proteins and organelles to scavenge amino acids, in a process termed autophagy (Klionsky, et al., *Science* 290: 1717 (2000); Kim, et al., *Annu. Rev. Biochem.* 69: 303 (2000); Klionsky, et al., *Annu. Rev. Cell Dev. Biol.* 15: 1 (1999)). Switching yeast cells to a poor carbon or nitrogen source induces a state of quiescence (G.sub.0). Similarly, rapamycin addition to yeast cultures or to mammalian cells in culture induces autophagy, even in a nutrient-rich medium (Noda, et al., *J. Biol. Chem.* 273: 3963 (1998); Blommaart, et al., *J. Biol Chem.* 270: 2320 (1995)). TOR signaling modulates gene expression via cytoplasmic sequestration of several nutrient-responsive transcription factors. TOR signals to several specific effectors (Tap42, Mks1p, Ure2p, Gln3p, and Gat1p) eliciting changes in the expression levels of enzymes involved in several different metabolic pathways (Shamji, et al., *Curr. Biol.* 10: 1574 (2000); Chan, et al., *PNAS USA* 97: 13227 (2000)). How TOR signaling may affect the transcription rates of metabolic enzymes in multicellular organisms has not yet been elucidated (Blommaart, et al., *J. Biol. Chem.* 270: 2320 (1995); Shigemitsu, et al., *J. Biol. Chem.* 274: 1058 (1999)).

In mammalian cells, autophagy is inhibited by amino acids and insulin. Activation of S6K is associated with inhibition of autophagy in rat hepatocytes, and the inhibition of autophagy by amino acids could be partially prevented by rapamycin treatment (Blommaart, et al., *J. Biol. Chem.* 270: 2320 (1995); Shigemitsu, et al., *J. Biol. Chem.* 274: 1058 (1999)).

The observation that rapamycin can inhibit long-term facilitation in Aplysia neurons has implicated TOR signaling in the control of neuronal protein synthesis (Casadio, et al., *Cell* 99: 221 (1999)). Several types of neurotransmitters were described to affect the activity of the rapamycin-sensitive pathway leading to S6K1 and 4E-BP1 phosphorylation. Serotonin (5-HT) addition to Aplysia neurons or Chinese hamster ovary (CHO) cells expressing the 5-HT1B receptor increases phosphorylation of S6K1 in a rapamycin-dependent manner (Khan, et al., *Neurosci.* 21: 382 (2001); Pullarkat, et al., *J. Neurochem.* 71: 1059 (1998)). Dopamine addition to CHO cells also activates S6K1 in a rapamycin-dependent manner (Welsh, et al., *J. Neurochem.* 70: 2139 (1998)). Finally, both S6K1 and 4E-BP1 phosphorylation is induced by stimulation of the μ-opioid receptors (which mediate the analgesic and addictive properties of morphine) by the agonist [D-Ala$^2$,N-MePhe$^4$,Gly$^5$-ol]enkephalin (DAMGO; Polakiewicz, et al., *J. Biol. Chem.* 273: 23534 (1998)). TOR interacts with gephyrin, a tubulin-binding protein involved in neuronal γ-aminobutyric acid type A (GABAA) and glycine receptor clustering (Sabatini, et al., *Science* 284: 1161 (1999); Scheper, et al., *J. Biol. Chem.* 267: 7269 (1992); Essrich, et al., *Nat. Neurosci.* 1: 563 (1998); Kirsch, et al., *Nature (London)* 366: 745(1993)). Gephyrin binding is reportedly required for signaling to S6K1 and 4E-BP1, and, consistent with a role in localized protein synthesis, a fractionation experiment demonstrated that TOR and gephyrin were enriched in the synaptosomal fraction but not in the post synaptosomal fraction (Sabatini, et al., *Science* 284: 1161 (1999)).

The role of TOR in the numerous signaling pathways listed above, as well as others, makes modulating TOR activity a potentially desirable treatment method for a variety of conditions. For example, TOR kinase activity is important for antigen-activated T-cell proliferation, thus, rapamycin, which inhibits TOR activity, is useful as an immunosuppressant. (Abraham et al., *Annu. Rev. Immuno.* 14: 483 (1996); Morice et al., *J. Biol Chem* 268: 3734 (1993)). Similarly, TOR has been identified as a therapeutic target involved in human cancers (Huang et al., *Current Opinion in Investigational Drugs*. 3(2):295 (2002)). However, there is a need in the art to fully understand the role of TOR in many signaling pathways, and to identify the various modulators of TOR kinase activity within these pathways. Such modulators, once identified, may be useful in treating many of the disorders associated with TOR signaling pathways.

A few TOR modulators, such as rapamycin, wortmannin and LY29004 have already been identified; however, the discovery of additional modulating agents is necessary to address the numerous conditions affected by TOR. However, current assays for screening for such agents rely on recombinant TOR, and produce, at best, poor results. For example, in mammalian cell lines, recombinant TOR yields are too low to be useful in any assay. Similarly, in bacterial cell lines, recombinant TOR is expressed in an insoluble form, and thus cannot be used in an assay. In addition, recombinant TOR, when expressed in insect cell lines, has no detectible kinase activity, and thus is not useful in any assays. Such limitations serve as a barrier to elucidating TOR's role in many signaling pathways and in identifying TOR modulators, which may be useful in treating the many disorders associated with TOR signaling. Thus, because of the limitations of recombinant TOR, there are no useful assays in the current art employing recombinant TOR. This is particularly true for high throughput screening assays, which are even less tolerant of recombinant TOR's limitations. Accordingly, there is a need in the current art for a TOR assay that measures TOR kinase activity, and that is adaptable to high throughput screening.

SUMMARY OF THE INVENTION

Thus, it is the design of this current invention to improve the art of screening for TOR modulating agents by providing a method using native TOR.

The present invention is directed to methods of screening for modulators of TOR phosphorylation activity. The methods may be used to detect modulators of TOR phosphorylation via phosphorylation of a TOR substrate.

The methods of the invention employ substrates comprising proteins whose serine/threonine residues are phosphorylated in a rapamycin-dependent manner in cells (Raught et al., *PNAS* 98: 7037 (2001); Abraham, *Cell* 111: 9 (2002); McMahon et al., *Mol. Cell. Biol.* 22: 7428 (2002)). The serine/threonine residues of the present invention respond to TOR's phosphorylation activity. The proteins of the invention include, but are not limited to fragments of P70 S6 Kinase lacking the kinase domain but containing Serine 371, Threonine 389 and Serine 404 fused to a GST tag (Patrick et al., *PNAS* 95: 1432 (1998); McMahon et al., *Mol. Cell. Biol.* 22: 7428 (2002)).

The methods of the invention also employ host cells that naturally express TOR proteins. Such host cells taught by the present invention include, but are not limited to, rat brain, unstripped (available from Pel-Freeze Biologics, Rogers Ariz., Cat #56004-2). Native TOR, as used in the current invention is isolated from these tissues.

According to the present invention, agents are screened for their ability to modulate TOR-mediated phosphorylation by comparing the level of TOR-mediated phosphorylation of a substrate determined in the presence vs. absence of the agent in the presence of TOR. Modulators discovered according to the present invention will modulate TOR activity in a given cellular or tissue context to treat TOR associated disorders. Such disorders include, but are not limited to autoimmune disorders, organ transplant inflammation, psoriasis, cancer, restenosis, and muscle wasting disorders.

In another aspect, a method for dissecting the signaling pathway for native TOR is provided. In this aspect one or more of the stages involved in the activation of TOR and in signaling pathways in which TOR is involved are modified. The effect of these modifications on TOR's phosphorylation activity is compared to unmodified pathways. For example, serum-starved cells are re-stimulated with fresh serum for times ranging from minutes to hours and semi-purified TOR can be prepared as described herein. The activation of TOR by serum (or polypeptide growth factors) results in a reproducible increase in the protein kinase activity, which is measured according to the protocol described below. Similarly, cells can be starved of glucose and amino acids, and activation of TOR by re-added single amino acids, glucose, or any combinations thereof can be assayed as described above. The investigator can then use standard genetic or pharmacological approaches to define the upstream events leading to the activation TOR. These studies could be used to define potential drug targets acting in the same pathway as rapamycin.

In a further aspect of the current invention, assays for detecting native TOR modulators and assays for dissecting native TOR signaling pathways are performed in high throughput. Such assays will employ a variety of high throughput screening techniques, preferably using a multi-well plate format.

BRIEF DESCRIPTION OF THE FIGURES

FIG. 1a. FIG. 1a is a western blot showing the absence or presence of recombinant TOR protein isolated from an S2 *drosophila melanogaster* cell line. pHybrid is the $CuSO_4$-inducible expression vector backbone used to create the mTOR expression constructs. In this sample line, results were obtained from cells transfected with the empty pHybrid vector only (no recombinant mTOR insert). mTOR.sup.wt is the recombinant TOR protein. mTOR.sup.KD is the recombinant TOR with an inactivated kinase domain. mTOR.sup..delta.958 is the recombinant TOR with an amino acid residue 958 deletion. FDC-PI-AU1mTOR is derived from stably transfected FDC-P1 cells (an IL3-responsive myeloid_cell line) that express the AU1-tagged recombinant mTOR protein. Lanes designated with a plus (+) represent cells treated with $CuSO_4$ to induce expression of the recombinant mTOR proteins. Lanes designated with a minus (−) include only the reaction reagents. Cupric Sulfate ($CuSO_4$) is used to induce expression of the recombinant mTOR constructs. The presence or absence of recombinant TOR in each lane was determined using a standard two-stage antibody western blot. Recombinant TOR is present only in the mTOR.sup.wt(+), mTOR.supKD(+), and mTOR.sup..delta.958(+) lanes FIG. 1b.

FIG. 2 is a bar chart of the assay results from Example 1 and Table 1. These results show that the TOR substrate P70 S6 kinase is phosphorylated when native TOR is present, but not when native TOR is absent or when heat inactivated TOR is present.

FIG. 3 is a bar chart representing the results from Example 3 and Table 3. These results show that wortmannin (Wn) is both an activator and an inhibitor of TOR kinase, depending on relative concentrations of kinase to wortmannin. Also shown in FIG. 4 is the inhibition of TOR kinase activity by rapamycin.

DEFINITIONS

Figure 1A:
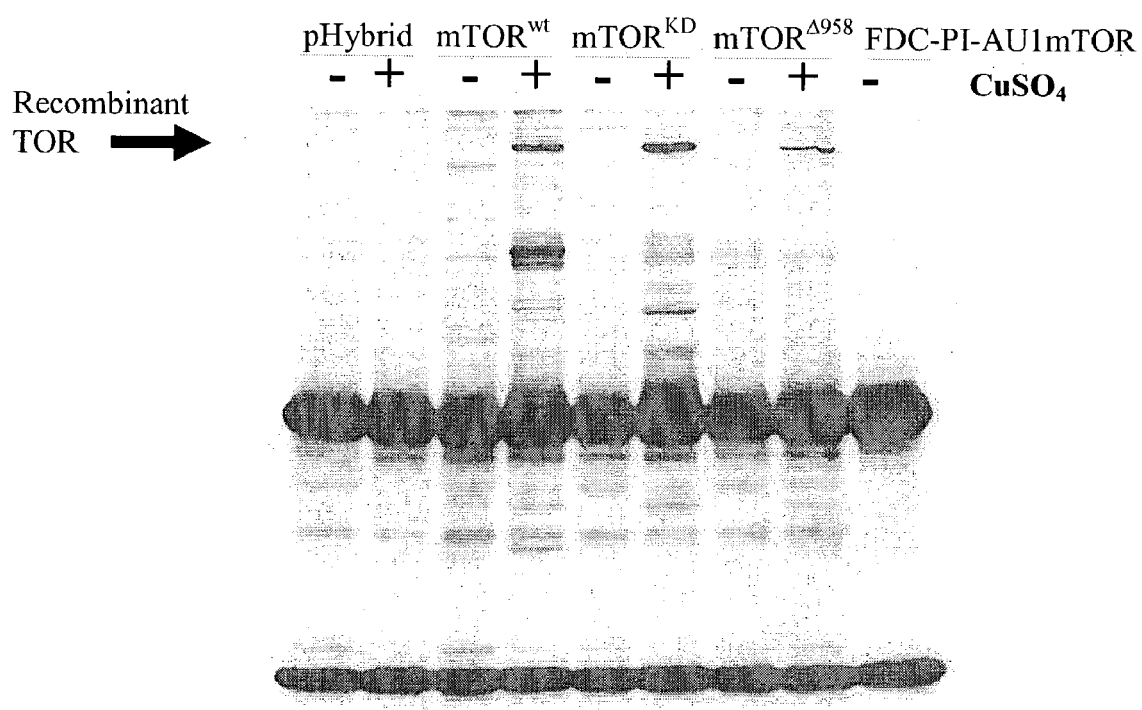

For the Purposes of This Invention:

"TOR" refers to a 280-300 kD peptide belonging to the phosphoinositide (PI) 3-kinase family, which phosphorylate proteins on serine or threonine residues. TOR is a highly conserved protein kinase found in both prokaryotes and eukaryotes. For example, Raught el al., *PNAS* 98: 7037 (2001) describe homologues of TOR protein found in *Saccharomyces cerevisiae, Schizosaccharomyces pombe, Drosophila melanogaster* and other Metazoans, and mammals. A single mammalian TOR protein has been cloned from several species. (Raught, et al., *PNAS* 98: 7037 (2001)). In a preferred embodiment, TOR is isolated from rat brain tissue using an ion-exchange column, and fraction purification. However, native TOR is easily isolated from a variety of tissues using a variety of techniques by those of skill in the art. By way of example only, bovine testes is another source for isolating native TOR protein. Additionally, one of skill in the art will readily isolate TOR proteins from other species for use within the spirit of the present invention. As used in the following description, "TOR" refers to any and all proteins in this described family, including but not limited to dTOR, mTOR, TOR1, TOR2, RAFT and others.

"Rapamycin" is a bacterial macrolide and a potent immunosuppressant with realized or potential clinical applications in the prevention of graft rejection after organ transplantation and the treatment of autoimmune disorders. This drug acts by forming a complex with the immunophillin FKBP12, and then inhibiting activity of TOR (Abraham et al., *Annu. Rev. Immuno.* 14: 483 (1996)). Rapamycin treatment of cells has been shown to lead to the dephosphorylation and inactivation of TOR substrates such as P70 S6 Kinase and 4E-BP1/PHAS1 (Dumont et al., *J. Immunol* 144: 251 (1990); Brown et al, *Nature* 369: 756 (1994); Kunz et al., *Cell* 73: 585 (1993); Jefferies et al., *EMBO J.* 15: 3693 (1997); Beretta et al., *EMBO J.*15: 658 (1996)). This makes rapamycin a useful probe for identifying the components of those pathways and determining their physiological roles.

"Wortmannin" is a potent, specific and direct inhibitor of PI3 kinase, originally derived from fungus. Inhibition is irreversible and non-competitive. (Nakanishi et al., *J. Biol. Chem.* 267: 2157 (1992); Arcaro et al., *Biochem. J.* 296: 297 (1993); Powis et al., *Cancer Res.* 54: 5241 (1994)). At high concentrations wortmannin is also a direct inhibitor of TOR and related kinases at higher drug concentrations (Brunn et al., *EMBO Journal.* 15(19): 5256 (1996); Sarkaria et al., *Cancer Research.* 58(19): 4375 (1998)).

"LY294002" is a highly selective inhibitor of PI3 kinase (Vlahos et al., *J. Biol. Chem.* 269: 5241 (1994)). LY294002 also directly inhibits TOR kinase activity (Brunn et al., *EMBO Journal.* 15(19): 5256 (1996))

"Modulator," as used herein, refers to a wide range of test agents, including, but not limited to natural, synthetic or semi-synthetic organic molecules, lipids, proteins, peptides, nucleotides, oligonucleotides and antisense nucleotide sequences, that directly influence the activity of TOR in phosphorylating a downstream agent. Furthermore, the precursor of a modulator (i.e., a agent that can be converted into a modulator) is also considered to be a modulator. Similarly, a agent which converts a precursor into a modulator is also considered to be a modulator. As readily recognized by those of skill in the art, a wide variety of test agents can be employed in the invention assays. Examples of agents contemplated for use in the practice of the present invention include, but are not limited to, rapamycin, wortmannin and LY294002.

"Substrate" refers to the proteins that are phosphorylated or regulated by TOR kinase. Substrates will possess a TOR preferred sequence motif, which may include but is not limited to serine/threonine residues followed by a proline or hydrophobic residue at the +1 position.

"Activate", "activated", "activation" or derivatives thereof, means the increase of TOR kinase activity on a substrate in the presence of a modulator.

"Inhibit", "inhibited", "inhibition" or derivatives thereof, means the decrease of TOR kinase activity on a substrate in the presence of a modulator.

DETAILED DESCRIPTION OF THE INVENTION

In one aspect, the present invention provides screening methods for agents which modulate native TOR phosphorylation activity resulting from the interaction of native TOR with a substrate, and identifying as modulators those test agents which substantially disrupt or enhance the phosphorylation of the substrate by native TOR. Suprisingly, the assay of the current invention wherein native TOR is used, possesses none of the stated limitations inherent in assays utilizing recombinant TOR.

Figure 1B:
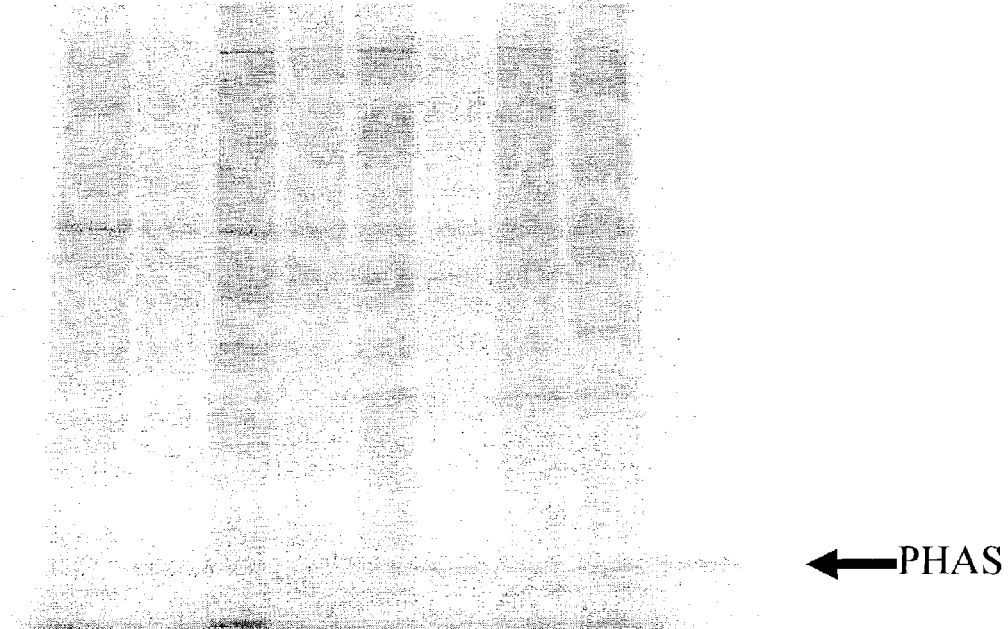
FIG. 1b is a phosphoimage measuring the kinase activity of the recombinant TOR proteins from FIG. 1a on a natural TOR substrate, PHAS-1. Recombinant TOR's ability to incorporate .sup.32P into PHAS-1 is shown at the bottom of the image. The TOR (+) well has no greater protein kinase activity that the sample containing empty vector (negative control) or the kinase-inactive $mTOR^{KD}$ mutant. Recombinant TOR has no detectable kinase activity.

As previously stated, recombinant TOR suffers from unusably low yields and inactive protein expression. For example, in FIGS. 1a and 1b, recombinant TOR is expressed in insect S2 cell lines, as shown by western immunoblot using a primary antibody raised against recombinant TOR. However, as shown by phosphoimaging, the recombinant TOR has no detectable kinase activity on the TOR substrate PHAS-1. Such results are typical for assays using recombinant TOR, and serve as a barrier to elucidating TOR's role in many signaling pathways and in identifying TOR modulators, which may be useful in treating the many disorders associated with TOR signaling.

Substrates used in the method of the current invention are those that are phosphorylated by TOR, and said phosphorylation by TOR being detectable. Preferably, TOR substrates having a phospho-specific antibody raised against their phosphorylated form are used in the assay. However, using alternative detection techniques well know in the art, other TOR substrates can be used in the current invention without loosing the spirit of the current invention.

Typically, TOR substrates are proteins bearing the PIKK preferred phosphorylation residues serine and/or threonine. Preferably, forms of the TOR substrate P70 S6 Kinase, which typically resides in the cytoplasm of a cell, are used in the described assay. Serine 371, Threonine 389 and Serine 404 are all residues of P70 S6 Kinase that are phosphorylated by TOR (McMahon et al., *Mol. Cell. Biol.* 22: 7428 (2002)). For the assay of the preferred embodiment herein, the P70 S6 Kinase residue Threonine 389 is phosphorylated in a rapamycin-dependant manner, and thus is measured to discover modulators according to the methods of the current invention. Those skilled in the art will readily employ the current invention method using a variety of TOR substrates and will measure TOR phosphorylation at any of a number of the substrate's serine/threonine residues.

In the preferred embodiment, a fragment of the substrate P70 S6 Kinase is used to detect agents that modulate the phosphorylation activity of TOR. Also in the preferred embodiment, P70 S6 Kinase is lacking the kinase domain. This fragment of P70 S6 Kinase is phosphorylated as efficiently as full-length P70 S6 Kinase by TOR (Burnett, et al., *PNAS USA* 95: 1432 (1998)). Those of ordinary skill in the art will readily adapt this method to other TOR substrates without loosing the spirit of the current invention.

The TOR substrate P70 S6 Kinase used in the current invention assay may be in solid phase or in suspension. Where assays are conducted in solid phase, one or more of the substrates of the assay are immobilized on a suitable support, which is then exposed to the other components of the assay. The phosphorylation of a substrate by TOR in the presence or absence of a test agent is then readily assayed in a variety of ways, as described in greater detail herein below.

Where assays are conducted in solution, all components are dissolved or suspended in suitable media. The phosphorylation of a substrate by TOR in the presence or absence of a test agent is then readily assayed in a variety of ways, as described in greater detail herein below.

In the preferred embodiment, TOR substrate is immobilized in solid phase for the assay. Methods for immobilizing a protein to a suitable support are well known in the art. One commonly practiced method employs a glutathione-S-transferase (GST) tag fused to one end of a protein (Smith et al., *Gene* 7: 31 (1988)). In brief, bacterial plasmid vectors are used for the synthesis of proteins which are "fused" together resulting in the creation of "fusion" proteins. An example of a fusion protein having a strong affinity for a known ligand is a GST fusion protein. GST fused proteins are easily immobilized on glutathione-bound plastic surfaces or beads through the interaction between the GST portion and its substrate, GSH. Glutathione is readily employed on numerous surfaces including, but not limited to Sepharose or agarose beads and reaction plate wells. Other well known immobilization techniques include, but are not limited to; using other well known tags, such as histidine, affinity chromatography techniques, immobilization through amine and carboxyl groups, and antibody capture, using for example GST-reactive antibodies. One of skill in the art will readily immobilize a variety of TOR substrates and their useful fragments using these and other well known techniques.

In the preferred embodiment of the current invention, a GST tag is fused to the P70 S6 Kinase fragment (GST~P70 S6K) using standard recombinant technologies. The pGEX-2T gene fusion system is readily available in the art (Amersham-Pharmacia, Piscataway, N.J., Cat#27-4801-01); however, other commercial systems are also readily available. Alternatively, those of ordinary skill in the art will produce fusion proteins useful in the current invention, without purchasing a commercially available kit. In the preferred embodiment a GST~P70S6K fusion protein was produced using pGEX-2T according to manufacturer's instructions, and the fusion protein is immobilized in a reaction well (Reacti-Bind Glutathione coated plates, Pierce, Rockford, Ill., Cat #15140). (see generally, Haystead et al., *J. Biol. Chem* 269: 23185 (1994); McMahon et al., *Mol. Cell. Biol*. 22: 7428 (2002); Sabers et al., *J. Biol. Chem*. 270: 815 (1995)). Immobilization of GST~P70 S6K to a glutathione coated plate is accomplished according to manufacturer instructions (Pierce, Rockford, Ill. Instructions set 0685w). Once GST~P70 S6K has been immobilized to the reaction well, a kinase reaction mixture is added.

A kinase reaction containing TOR elution product in the presence or absence of an agent was prepared. As discussed above, TOR is a highly conserved protein found in both prokaryotes and eukaryotes. In a preferred embodiment of the current invention, TOR is isolated from eukaryotic tissues, more preferably from mammalian tissue and most preferably from rat brain tissue; however, those of ordinary skill in the art will readily isolate native TOR from any species possessing this protein or its homologues. By way of example only, bovine testes are another source for isolating native TOR protein.

Methods for isolating native protein from tissues are well known in the art and include, but are not limited to, affinity chromatography, antibody capture and precipitation with TOR-interacting GST fusion proteins immobilized on beads. In the preferred embodiment, TOR is isolated from rat brain extract using a sulphopropyl group ion exchange column, according to manufacturer's procedure (Amersham Biosciences, Piscataway, N.J., Cat #71-0729-10). Fractions are analyzed for the presence of TOR using standard immunoblotting techniques, and the purest TOR fractions were resuspended in 30% glycerol.

Semi-pure TOR fractions isolated from mammalian tissues are used in the kinase assay without further purification. Further purification causes a loss of activity. Kinase assays containing the highly specific TOR kinase inhibitor, FKBP12~rapamycin result in a complete loss of kinase activity, as discussed further below. Thus, the measured kinase activity of the current invention is only TOR kinase activity, as shown by TOR specific inhibition. TOR's catalytic, regulatory and binding domains have been well characterized in the art, and TOR fragments containing these necessary TOR domains are readily prepared by those of ordinary skill in the art. In the preferred embodiment of the current invention; however, the native TOR is preferably whole protein from the elution fraction.

Kinase assays are performed in reaction wells containing immobilized GST~P70 S6K, and comprise TOR− reaction wells, TOR+ reaction wells, heat inactivated TOR reaction wells (heat at 65.degree. C. for one hour) and may additionally contain TOR−/test agent reaction wells or TOR+/test agent reaction wells. Positive control wells for determining maximum detectable fluorescence may also be included in the kinase assay. A variety of kinase assays are well known to those of ordinary skill in the art, and fall well within the spirit of the current invention.

In the preferred embodiment, kinase reaction mixtures contain a 2× Kinase buffer (0.1 mM ATP, 20 mM $MnCl_2$, 20 mM HEPES pH 7.4, 20 mM beta-glycerophosphate, 100 nM microcystin, 1 mM EDTA, and 2 mM DTT). The 2 mM DTT (Dithiothreitol) is removed from kinase reaction mixtures testing agents known to be unstable in the presence of sulfhydryl-reducing agents. Depending on the agent tested and/or the substrate used in the reaction, other sulfide reducing protein chemistry methods are effectively employed by those of skill in the art; for example, alkylation of sulfhydryls with beta-mercaptoethanol.

Kinase reaction wells are loaded in equal volume with kinase buffer and either with TOR kinase in the presence or absence of a test agent, with heat inactivated TOR, or with test agent, only. TOR− reaction wells contain an equal volume of water to kinase buffer; thus omitting TOR. Kinase reactions are carried out according to standard procedure such as that described in Brunn et al, *J. Biol. Chem*. 272(51): 32547 (1997); and Brunn et al., *Science*. 277(5322): 99 (1997); however, those of ordinary skill in the art will readily employ these and other kinase reaction methods achieving the same results.

Preferably, TOR-mediated phosphorylation of GST~P70 S6K at residue threonine 389 is detected using a two stage antibody detection system. First stage antibody is raised in rabbit against phospho-threonine 389 containing P70 S6 Kinase. Second stage antibody is raised against the first and further bears a covalently linked enzyme that allows detection of the phospho-specific antibody when bound to the immobilized mTOR substrate. Alternatively, antibodies raised against phospho-threonine 389 containing P70 S6 Kinase are readily available from vendors such as Cell Signaling Technology, (Beverly, Mass., Cat #9205). Those of ordinary skill in the art will readily employ a variety of common methods in detecting TOR mediated phosphorylation of the substrate; including, but not limited to first stage antibodies raised against the TOR~substrate complex, or radiolabelled second stage antibodies. These and other modifications are well within the spirit of the current invention.

For reaction wells designated as positive controls, a two-stage antibody detection system is raised against the GST/TOR complex for determining maximum possible phosphorylation in the reaction. This system detects TOR-bound GST~P70 S6K, determining the maximum amount of detectible fluorescence. In this system the primary antibody is raised against GST/TOR, and the secondary antibody is raised against the first and further bears a detectable, covalently linked enzyme. Similar to the detection method for TOR phosphorylation of a substrate, one of ordinary skill in the art will readily employ a variety of methods for detecting TOR bound substrate.

In the preferred embodiment, phosphorylation of the substrate (or bound substrate for the positive reaction wells) is determined using a fluorogenic peroxidase reaction, and the relative fluorescent units (RFU) are read on a luminometer. In general, the detection reaction is as follows: (1) invert plate to empty wells and blot plate three times on a stack of paper towels; (2) incubate 50–100 μl of horseradish peroxidase conjugate in each well for 1 hour at room temperature; (3) invert plate to empty wells and blot plate three times on a stack of paper towels; (4) add 100 μl of QuantaBlu Fluorogenic Peroxidase to each well and incubate for 1.5–90 minutes at 37.degree.C.; and (5) read on a luminometer. The excitation and emission maxima for QuantaBlu Fluorogenic Peroxide Substrate are 325 nm and 420 nm, respectively. Wavelengths between 315 and 340 nm for excitation and 370 and 470 nm for emission also can be used for detection. QuantaBlu Fluorogenic Peroxidase reaction kits are available from Pierce, Rockford, Ill., (Cat #15169); however, a variety of commercial equivalents are readily available. Additionally, those of ordinary skill in the art will readily design reagents for detection reactions.

According to the invention, TOR responsive substrates can be used to detect modulators of the TOR phosphorylation activity. In detecting modulators of TOR's phosphorylation activity, the level of phosphorylation of one or more TOR substrate proteins is measured (1) in the presence of both TOR and a test agent, and (2) in the presence of TOR alone, and the measurements are compared. TOR modulators are identified as those agents which alter the phosphorylation of a substrate protein by TOR. Thus any agent which alters the level of substrate phosphorylation by TOR is identified as a TOR modulator. Those agents which increase the level of substrate phosphorylation by TOR are identified as activators of TOR and those which decrease the level of substrate phosphorylation by TOR are identified as inhibitors of TOR. One example of such a modulating agent is rapamycin (discussed above. See; Dumont et al., *J. Immonol* 144: 251 (1990); Brown et al, *Nature* 369: 756 (1994); Kunz et al., *Cell* 73: 585 (1993); Jefferies et al., *EMBO J.* 15: 3693 (1997); Beretta et al., *EMBO J.* 15: 658 (1996)).

In a preferred embodiment, high throughput screening (HTS) systems are used to detect TOR kinase modulators. Such systems preferably include the use of robotic systems. The assays of the present invention offer the advantage that many samples can be processed in a short period of time. For example, plates having 96, 384, 1536 or as many wells as are commercially available can be used.

High throughput screening systems are commercially available (see, e.g., Zymark Corp., Hopkinton, Mass.; Air Technical Industries, Mentor, Ohio; Beckman Instruments, Inc., Fullerton, Calif.; Precision Systems, Inc., Natick, Mass., etc.) These systems typically automate entire procedures including all sample and reagent pipetting, liquid dispensing, timed incubations, and final readings of the microplate in detector(s) appropriate for the assay. These configurable systems provide high throughput and rapid start up as well as a high degree of flexibility and customization. The manufacturers of such systems, i.e., Zymark Corp., provide detailed protocols for the various high throughput assays.

Generally, a plurality of assay mixtures are run in parallel each having different kinase reaction mixtures, including TOR negative and TOR positive with or without the varying candidate agents. In one preferred embodiment, high throughput screening methods involve providing a library containing a large number of candidate agents potentially having the desired activity. Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics compounds.

For example, in one embodiment, candidate agents are assayed in highly parallel fashion by using multiwell plates by placing a kinase reaction mixture containing TOR alone or TOR and one of the many candidate agents in the wells of the multiwell plate. Assays are performed as described herein and the absorbance or fluorescence of each well of the plate can be measured by a plate reader. A candidate agent which modulates the function of TOR kinase is identified by an increase or decrease in the rate substrate phosphorylation compared to a control assay in the absence of that candidate agent.

A number of alternative types of assay and schemes can be utilized for detection in the methods of the present invention. One example, is a coloriametric assay performed with a substrate that generates color rather than fluorescence. Such assays are well known in the art. Accordingly, the secondary antibody, as described above, may couple with a biotin based color detection system or a radiolabel detection system.

Alternatively the ability of a test agent to modulate TOR kinase activity can be measured by assessing the degree of TOR mediated phosphorylation using radiolabelled ATP as the phosphate donor. In a version of this assay, [.gamma.-.sup.32P]ATP is incorporated into into the substrate by TOR. Relative amounts of .sup.32P are detected using sodium dodecyl sulfate-polyacrylamide gel electrophoresis (SDS-PAGE) followed by phosphoimaging. Absolute amounts of .sup.32P are determined by slicing the phosphorylated substrate out of the SDS-PAGE gel and subjecting them to scintillation counting (McMahon et al., *Mol. Cell. Biol.* 22: 7428 (2002)). One of ordinary skill in the art will readily employ known detection techniques for determining TOR kinase activity, all within the spirit of the current invention.

Alternatively, for use with soluble substrate reactions western immunoblotting is an effective assay. Western immunoblotting is well known in the art (See; Towbin, et al., PNAS 76: 4350 (1979); Harlow, et al., Immunoblotting. In Antibodies: A Laboratory Manual, Cold Spring Harbor Laboratory, New York, pp. 471–510 (1988); Bjerrum, et al., CRC Handbook of Immunoblotting of Proteins, Vol. 1, pp. 227–254 (1988); Dunbar, B. ed., Protein Blotting: A Practical Approach, IRL/Oxford University Press (1994); and Coligan et al., eds., Current Protocols in Immunology, John Wiley & Sons, Inc. (1994)). In general, the ability of a test agent to modulate TOR kinase activity can be measured by assessing the degree to which the test agent alters TOR mediated phosphorylation of a substrate using a two stage antibody raised against the TOR-phosphorylated substrate, or in the alternative raised against the TOR-bound substrate. Kinase reactions are first separated using sodium dodecyl sulfate-polyacrylamide gel electrophoresis. Proteins are then transferred from the gel to a membrane. The membrane bound protein are blocked, washed and exposed to primary and secondary antibody as described above. Detection methods include enzyme linked fluorescence, scintillation counting, or any other method well known to those of skill in the art.

Modulators identified by the methods of the current invention may be used as drugs for modulating the activity of TOR. Any agent modulating the TOR kinase activity may be useful for treating or preventing a variety of conditions including, but not limited to: muscle wasting disorders like Multiple Sclerosis; cancer; psoriasis; auto-immune disorders; inflammation; organ transplant rejection; and restenosis following implant of arterial stents. (Saunders et al., *Kidney Int.*, 59: 3 (2001); Hidalgo et al., *Oncogene* 19: 6680 (2000); Sousa et al., *Circulation* 104: 2007 (2001)).

Once identified as a TOR modulator using a method of the current invention, an agent can be put in a pharmaceutically acceptable formulation, such as those described in Remington's Pharmaceutical Sciences, 18th ed., Mack Publishing Co., Easton, Pa. (1990), incorporated by reference herein, to generate a pharmaceutical composition useful for specific treatment of diseases and pathological conditions.

Agents identified by the methods taught herein can be administered to a patient either by themselves, or in pharmaceutical compositions where it is mixed with suitable carriers or excipient(s). In treating a patient exhibiting a disorder of interest, a therapeutically effective amount of agent or agents such as these is administered. A therapeutically effective dose refers to that amount of the agent that results in amelioration of symptoms or a prolongation of survival in a patient.

The agents also can be prepared as pharmaceutically acceptable salts. Examples of pharmaceutically acceptable salts include, but are not limited to acid addition salts such as those containing hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate. Such salts can be derived using acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid.

Pharmaceutically acceptable salts can be prepared by standard techniques. For example, the free base form of the agent is first dissolved in a suitable solvent such as an aqueous or aqueous-alcohol solution, containing the appropriate acid. The salt is then isolated by evaporating the solution. In another example, the salt is prepared by reacting the free base and acid in an organic solvent.

Carriers or excipients can be used to facilitate administration of the agent, for example, to increase the solubility of the agent. Examples of carriers and excipients include calcium carbonate, calcium phosphate, various sugars or types of starch, cellulose derivatives, gelatin, vegetable oils, polyethylene glycols and physiologically compatible solvents.

Toxicity and therapeutic efficacy of such agents can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Agents which exhibit large therapeutic indices are preferred. The data obtained from these cell culture assays and animal studies can be used in formulating a range of dosage for use in humans. The dosage of such agents lies preferably within a range of circulating concentrations that include the $ED_{50}$ with little or no toxicity. The dosage may vary within this range depending upon the dosage form employed and the route of administration utilized.

For any agent identified by the methods taught herein, the therapeutically effective dose can be estimated initially from cell culture assays. For example, a dose can be formulated in animal models to achieve a circulating plasma concentration range that includes the $IC_{50}$ as determined in cell culture (i.e., the concentration of the test agent which achieves a half-maximal disruption of the protein complex, or a half-maximal inhibition of the cellular level and/or activity of a complex component). Such information can be used to more accurately determine useful doses in humans. Levels in plasma may be measured, for example, by HPLC.

The exact formulation, route of administration and dosage can be chosen by the individual physician in view of the patient's condition. (See e.g. Fingl et al., in *The Pharmacological Basis of Therapeutics*, Ch. 1 p. 1 (1975)). It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. Techniques for formulation and administration may be found in *Remington's Pharmaceutical Sciences*, 18th ed., Mack Publishing Co., Easton, Pa. (1990). Suitable routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections, just to name a few.

For injection, the agents may be formulated in aqueous solutions, preferably in physiologically compatible buffers such as Hanks's solution, Ringer's solution, or physiological saline buffer. For such transmucosal administration, penetrants appropriate to the barrier to be permeated are used in the formulation. Such penetrants are generally known in the art.

Use of pharmaceutically acceptable carriers to formulate the agents herein disclosed into dosages suitable for systemic administration is contemplated. With proper choice of carrier and suitable manufacturing practice, these agents, in particular, those formulated as solutions, may be administered parenterally, such as by intravenous injection. The agents can be formulated readily using pharmaceutically acceptable carriers well known in the art into dosages suitable for oral administration. Such carriers enable the agents of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are efficiently delivered into the cell cytoplasm. Additionally, due to their hydrophobicity, small organic molecules may be directly administered intracellularly.

Pharmaceutical compositions suitable for use in the context of the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active agents into preparations which can be used pharmaceutically. The preparations formulated for oral administration may be in the form of tablets, dragees, capsules, or solutions. The pharmaceutical compositions contemplated by the present invention may be manufactured in a manner that is itself known, e.g., by means of conventional mixing, dissolving, granulating, dragee-making, levitating, emulsifying, encapsulating, entrapping or lyophilizing processes.

Pharmaceutical formulations for parenteral administration include aqueous solutions of the active agents in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the agents to allow for the preparation of highly concentrated solutions.

Pharmaceutical preparations for oral use can be obtained by combining the active agents with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agent doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active agents may be dissolved or suspended in suitable liquids, such as fatty oils, liquid paraffin, or liquid polyethylene glycols. In addition, stabilizers may be added.

Some methods of delivery that may be used include:
a. encapsulation in liposomes,
b. transduction by retroviral vectors,
c. localization to nuclear compartment utilizing nuclear targeting site found on most nuclear proteins,
d. transfection of cells ex vivo with subsequent reimplantation or administration of the transfected cells,
e. a DNA transporter system.

In another aspect, a method for dissecting the signaling pathway for native TOR is provided. In this aspect one or more of the stages involved in the activation of TOR and in signaling pathways in which TOR is involved are modified. The effect of these modifications on TOR's phosphorylation activity is compared to unmodified pathways. For example, serum-starved cells are re-stimulated with fresh serum for times ranging from minutes to hours and semi-purified TOR can be prepared as described herein. The activation of TOR by serum (or polypeptide growth factors) results in a reproducible increase in the protein kinase activity, which is measured according to the protocol described below. Similarly, cells can be starved of glucose and amino acids, and activation of TOR by re-added single amino acids, glucose, or any combinations thereof can be assayed as described above. The investigator can then use standard genetic or pharmacological approaches to define the upstream events leading to the activation TOR. These studies could be used to define potential drug targets acting in the same pathway as rapamycin.

The invention will be further illustrated by reference to the following non-limiting Examples.

EXAMPLE 1

Purification of TOR

The source of the enzyme is rat brain extract prepared as described in Sabers et al., *J. Biol. Chem* 270(2): 815 (1995). Briefly, whole rat brains (Pel-Freeze code 56004-2) were homogenized in extraction buffer (50 mM Tris pH 7.4, 100 mM NaCl, 10% glycerol, supplemented with protease inhibitors [1 mM PMSF, 10 µg/ml leupeptin, 5 µg/ml aprotinin, 1 µg/ml pepstatin] 1 mM MgCl$_2$, 1 mM CaCl$_2$, 15 mM β-glycerophosphate, and 2 mM β-mercaptoethanol). Five ml of supplemented extraction buffer was used per whole brain. The brains were homogenized with a Polytron™ tissue grinder (setting 5 until all visible tissue fragments were gone, and then a 10 second burst at setting 7). Homogenization is performed on a bed of wet ice. The lysate was centrifuged for 20 minutes at 10,000×g, and the insoluble pellet discarded. The supernatant was removed and re-centrifuged for 1 hour at 100,000×g. The soluble material was removed and brought to 30% saturation with (NH$_4$)$_2$SO$_4$ with continuous stirring on ice. After 10 minutes, the mixture was centrifuged for 20 min at 10,000×g, the supernate discarded, and the pellet resuspended supplemented extraction buffer (2 ml per whole brain). The soluble protein was dialyzed overnight against 50 mM Tris pH 7.4, 100 mM NaCl, 10% glycerol. If insoluble material appears after dialysis, it is removed by centrifugation at 10,000×g. Protein is measured using a standard Bio-Rad.sup.TM Protein Assay kit (Hercules, Calif., e.g., Cat #500-0001). The clarified material is called "rat brain extract", and is aliquoted and stored at −80° C.

Two milligrams of rat brain extract protein was diluted with 6 volumes of Buffer 1 (10 mM TrispH 8.0, 16 mM NaCl, 1 mM DTT, 1 mM EDTA, 1 mM PMSF, 10 µg/ml leupeptin, 5 µg/ml aprotinin, 1 µ/ml pepstatin, 0.1% Tween20) and run through a 0.5 ml bed-volume SP Sepharose Fast Flow (Amersham Biosciences, Piscataway, N.J., Cat #17-0729-10) column. The column was first washed with 25 column volumes of Buffer 1, then with 2 volumes of Buffer 2 (10 mM Tris pH 8.0, 50 mM NaCl, 1 mM DTT, 1 mM EDTA, 10 µg/ml leupeptin, 5 µg/ml aprotinin, 1 µg/ml pepstatin, 0.1% Tween20) and finally eluted with 3 volumes of Buffer 3 (10 mM Tris pH 8.0, 150 mM NaCi, 1 mM DTT, 1 mM EDTA, 10 µg/ml leupeptin, 5 µg/ml aprotinin, 1 µg/ml pepstatin, 0.1% Tween20), which yielded the cleanest TOR fraction as visualized by immunoblotting. Glycerol was added to 30% final concentration and samples were stored at −80° C.

Substrate Bearing Reaction Plates

Five hundred nanograms of a GST fusion peptide of the protein p70 S6 Kinase containing the phospho-acceptor Threonine 389 (Thr389) was bound to Reacti-Bind Glutathione coated strip-well plates (Pierce #15140) for one hour. Wells were then washed 3 times with wash buffer (1×PBS, 0.05% Tween20).

Kinase Assay

Fifty microliters of TOR elution fraction is combined with 50 µl of 2× Kinase buffer (0.1 mM ATP, 20 mM MnCl2, 20 mM HEPES pH 7.4, 20 mM β-glycerophosphate, 100 nM microcystin, 1 mM EDTA, 2 mM DTT). Background, positive and denatured enzyme (heat at 65° C. for 1 hour) controls were also performed. The reaction was carried out at 30° C. for 50 minutes and then stopped by washing the plates 3 times with wash buffer.

Detection

Phosphorylation of the Thr389 residue of P70 S6 Kinase by TOR is detected using a phospho-p70 S6 Kinase (Thr389) primary antibody and an enzyme linked secondary anti rabbit IgG antibody. The fluorogenic peroxidase reaction was performed for 60 minutes at 37° C. with the QuantaBlu Fluorogenic peroxidase substrate (Pierce, Rockford, Ill., Cat #15169). Relative fluorescent units (RFU) are read at 325 nm and 420 nm on a luminometer.

RESULTS

Figure 2:
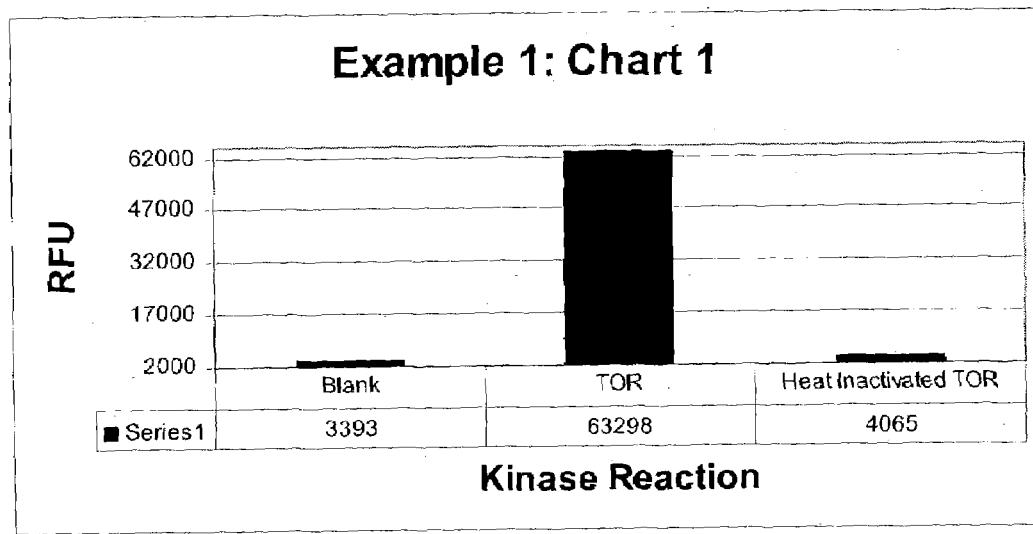
FIG. 2.
Figure 3:
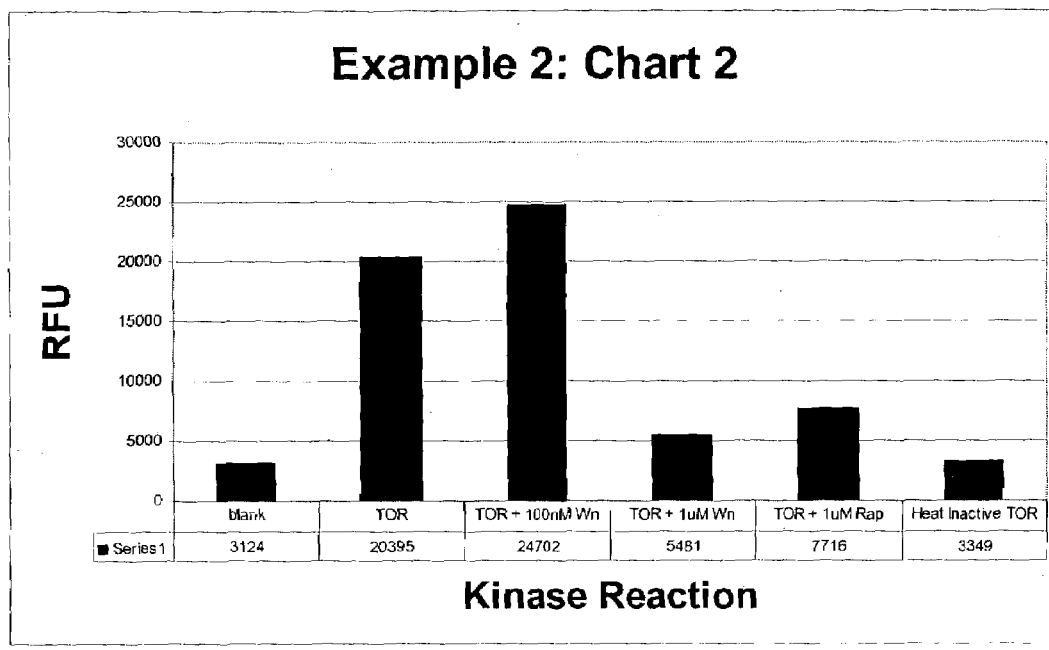
FIG. 3.

As seen in table 1 and FIG. 2, substrate P70 S6 Kinase is phosphorylated at residue threonine 389 by TOR kinase.

TABLE 1

Base-line RFU

| Sample | Fluorescence (RFU) |
|---|---|
| Blank | 3393 |
| TOR | 63298 |
| Heat Inactivated TOR | 4065 |

EXAMPLE 2

Purification of TOR

Native TOR was purified according to the procedure detailed in Example 1, above.

Substrate Bearing Reaction Plates

TOR substrate bearing plates were prepared according to the procedure detailed in Example 1, above.

Kinase Assay

Fifty microliters of TOR elution fraction is combined with 50 µl of 2× Kinase buffer (0.1 mM ATP, 20 mM MnCl2, 20 mM HEPES pH 7.4, 20 mM β-glycerophosphate, 100 nM microcystin, 1 mM EDTA, 2 mM DTT). Test agent reactions comprised 50 µl of a TOR elution fraction containing either 100 nM Wortmannin, 1 µM Wortmannin or 1 µM rapamycin combined with 50 µl of 2× Kinase buffer (0.1 mM ATP, 20 mM MnCl2, 20 mM HEPES pH 7.4, 20 mM β-glycerophosphate, 100 nM microcystine, 1 mM EDTA, 2 mM DTT). For reaction mixtures containing the agent wortmannin, DTT was ommitted from the reaction mixture. Background and enzyme dead (heat at 65.degree. C. for 1 hour) controls were also performed. The reaction was carried out at 30.degree.C. for 60 minutes and then stopped by washing the plates 3 times with wash buffer.

Detection

Phosphorylation of the Thr389 residue of P70 S6 Kinase by TOR is detected using a phospho-p70 S6 Kinase (Thr389) primary antibody and an enzyme linked secondary antibody. The fluorogenic peroxidase reaction was performed for 60 minutes at 37.degree. C. with the QuantaBlu Fluorogenic peroxidase substrate (Pierce #15169). Relative fluorescent units (RFU) are read at 325 nm and 420 nm on a luminometer.

Results

As seen in table 3 and FIG. 4, wortmannin is a concentration-dependant inhibitor of TOR mediated phosphorylation of the substrate P70 S6 Kinase. Rapamycin is a potent inhibitor of TOR mediated phosphorylation of the substrate P70 S6 Kinase.

TABLE 2

Effects of Wortmannin and Rapamycin on TOR Activity

| Sample | Fluorescence (RFU) |
|---|---|
| blank | 3124 |
| TOR | 20395 |
| TOR + 100 nM Wn | 24702 |
| TOR + 1 uM Wn | 5481 |
| TOR + 1 uM Rap | 7716 |
| Heat Inactive TOR | 3349 |

These data document the novel finding that modulators of TOR are detected in assays using native TOR with much greater sensitivity and specificity than in assays using recombinant TOR. Agents shown to modulate TOR by the current invention are useful in developing treatments for a wide range of disorders involving TOR kinase activity. Furthermore, the assay of the current invention is useful in dissection of the TOR signaling pathway.

All publications referenced are incorporated by reference herein, including the nucleic acid sequences and amino acid sequences listed in each publication. All the agents reference herein, including those agents disclosed and referred to in articles cited by the publications mentioned above.

Although the invention has been described with reference to the disclosed embodiments, those skilled in the art will readily appreciate that the specific experiments detailed are only illustrative of the invention. It should be understood that various modifications can be made without departing from that spirit of the invention.

The invention claimed is:

1. A method of identifying an agent that modulates the phosphorylation activity of a Target of Rapamycin (TOR) protein, comprising the steps of:
   (a) extracting and partially purifying native TOR from a host cell;
   (b) contacting the TOR protein and a substrate of TOR under conditions that allow TOR's phosphorylation activity on said substrate;
   (c) detecting phosphorylation activity;
   (d) adding the agent to the TOR protein and the TOR substrate;
   (e) detecting phosphorylation activity;
   (f) determining an agent's modulation of TOR's phosphorylation activity by comparing the change in said activity to TOR's phosphorylation activity in the absence of said agent; and
   (g) correlating the change in TOR's phosphorylation activity with the agent being one that modulates said activity;
with the proviso that the Target of Rapamycin protein is not recombinant.

2. The method of claim 1 wherein said host cell is a mammalian cell.

3. The method of claim 2 wherein said host cell is a rat cell.

4. The method of claim 3 wherein said host cell is a brain cell.

5. The method of claim 1 wherein said substrate is a fusion protein.

6. The method of claim 5 wherein said substrate is selected from the group consisting of p70 S6 Kinase and 4E-BP1.

7. The method of claim 6 wherein said substrate further comprises a phospho-acceptor site.

8. The method of claim 7 wherein said substrate further comprises the phosphor-acceptor residue threonine 389.

9. The method of claim 1 wherein said detection of phosphorylation is quantitative.

10. The method of claim 9 wherein said detection of phosphorylation is done using two-stage enzyme linked antibodies.

11. The method of claim 1 wherein said agent that modulates the phosphorylation activity of TOR is identified in a high throughput screening format.

* * * * *